(12) United States Patent
Livesay et al.

(10) Patent No.: US 11,908,552 B2
(45) Date of Patent: Feb. 20, 2024

(54) METHODS FOR QUALITY DATA EXTRACTION, ALIGNMENT, AND REPORTING

(71) Applicant: Michigan Health Information Network Shared Services, East Lansing, MI (US)

(72) Inventors: Jeff Livesay, Pinckney, MI (US); Tim Pletcher, Mount Pleasant, MI (US)

(73) Assignee: Michigan Health Information Network Shared Services, East Lansing, MI (US)

( * ) Notice: Subject to any disclaimer, the term of this patent is extended or adjusted under 35 U.S.C. 154(b) by 109 days.

(21) Appl. No.: 15/982,920

(22) Filed: May 17, 2018

(65) Prior Publication Data

US 2018/0268928 A1    Sep. 20, 2018

Related U.S. Application Data

(63) Continuation of application No. 15/690,057, filed on Aug. 29, 2017, now abandoned.

(60) Provisional application No. 62/380,689, filed on Aug. 29, 2016.

(51) Int. Cl.
| | |
|---|---|
| *G16H 10/60* | (2018.01) |
| *G16H 40/20* | (2018.01) |
| *G16H 50/30* | (2018.01) |
| *G16H 15/00* | (2018.01) |

(52) U.S. Cl.
CPC ............ *G16H 10/60* (2018.01); *G16H 15/00* (2018.01); *G16H 40/20* (2018.01); *G16H 50/30* (2018.01)

(58) Field of Classification Search
CPC ........ G16H 10/60; G16H 15/00; G16H 40/20; G16H 50/30
See application file for complete search history.

(56) References Cited

U.S. PATENT DOCUMENTS

| | | | |
|---|---|---|---|
| 5,155,802 A | 10/1992 | Mueller et al. | |
| 5,804,373 A | 9/1998 | Schweitzer et al. | |
| 7,668,820 B2* | 2/2010 | Zuleba | G06F 21/6227 707/765 |
| 8,688,476 B2* | 4/2014 | Cinqualbre | G16H 10/60 705/3 |
| 2001/0032099 A1 | 10/2001 | Joao | |
| 2006/0161456 A1* | 7/2006 | Baker | G06Q 50/22 705/2 |

(Continued)

OTHER PUBLICATIONS

International Search Report and Written Opinion issued on PCT/US2017/049184, dated Nov. 3, 2017.

*Primary Examiner* — Eliza A Lam
(74) *Attorney, Agent, or Firm* — Honigman LLP

(57) ABSTRACT

A method according to a set of instructions stored on the memory of a computing device includes receiving from a plurality of measure storage devices, by a processor of the computing device, a plurality of measures pertaining to at least one patient and at least one clinical measure of the at least one patient. The plurality of measure storage devices are associated with at least one of a plurality of healthcare providers. The method further includes determining, by the processor, a patient-centered quality measure indicating quality across the plurality of healthcare providers with respect to the at least one patient and the at least one clinical measure.

20 Claims, 5 Drawing Sheets

(56) References Cited

U.S. PATENT DOCUMENTS

| | | | |
|---|---|---|---|
| 2008/0065419 A1* | 3/2008 | Esseiva | G16H 10/65 709/201 |
| 2008/0196108 A1* | 8/2008 | Dent | G06F 17/30592 726/28 |
| 2009/0063189 A1* | 3/2009 | Hupke | G16H 10/20 382/209 |
| 2012/0303381 A1* | 11/2012 | Bessette | A61B 5/00 705/2 |
| 2013/0191157 A1 | 7/2013 | Eiden et al. | |
| 2013/0332194 A1 | 12/2013 | D'Auria et al. | |
| 2014/0039920 A1* | 2/2014 | Nadai | G06Q 10/087 705/2 |
| 2014/0316810 A1* | 10/2014 | Oliver | G06F 19/322 705/3 |
| 2014/0349262 A1* | 11/2014 | Mason | G09B 19/00 434/236 |
| 2015/0128287 A1* | 5/2015 | LaFever | G06F 21/6254 726/27 |
| 2015/0347705 A1 | 12/2015 | Simon et al. | |
| 2016/0125142 A1 | 5/2016 | Awad | |
| 2016/0267115 A1 | 9/2016 | Pletcher et al. | |
| 2018/0060497 A1 | 3/2018 | Livesay et al. | |

* cited by examiner

METHODS FOR QUALITY DATA EXTRACTION, ALIGNMENT, AND REPORTING

CROSS REFERENCE TO RELATED APPLICATION

This application is a Continuation Application of U.S. patent application Ser. No. 15/690,057 filed Aug. 29, 2017, which claims priority to U.S. Provisional Application 62/380,689 filed on Aug. 29, 2016, each of which is incorporated herein by reference in its entirety.

BACKGROUND

Measuring quantifiable data is widely practiced throughout the world. Measurements can be used in many various industries and for many various purposes. For example, measurements may be utilized in industries such as health care, banking, finance, retail, services, or any other industry. Measurements may also be kept or stored in various ways. For example, measurements may be stored physically in files or electronically on cloud storages, document management systems, secure servers, hard drives, etc.

In just one example, measurements are utilized in the health care industry for various purposes. For example, a health care provider may measure a patient's vitals, presence of chemicals, or any other type of measurement. Such measurements may be used to understand a patient's health, and may be further used by an insurance provider of the patient or another third party payee such as a government agency.

Measurements are important to many individuals, businesses, and governments. Accordingly, measurements are the subject of much attention with regards to how measurements are identified, aggregated, classified, prioritized, stored, secured, archived, preserved, retrieved, tracked, destroyed, and otherwise used. Decisions based on such measurements are made based on many different factors including applicable laws, company policies, expected future utilization of a measurement, type of measurement, importance/value of a measurement, etc.

Heretofore, conventional healthcare delivery and payment systems are volume-based in that the more volume a physician or medical care provider has, the higher their reimbursement. Rewarding physicians or other medical providers for volume instead of quality of outcome results in unwanted and inefficient outcomes. In an effort to shift quality based delivery, federal and state governments are requiring quality reporting on quality measures. Such reporting may include hundreds of quality measures.

Another challenge with conventional healthcare delivery and payment systems includes reporting measures that are "provider-centric" which assess provider performance on the measures reported. This provider-centric approach does not necessarily correlate to improved outcomes for patients. In fact, the provider-centric approach enables providers and clinics to "game" the system to report high "scores" on their quality measures to insure maximum financial reward regardless of the outcome for the patient under today's quality reporting approach. Further, conventional "provider-centric" quality measuring and reporting typically involves the actions of only one provider in one care setting for each patient whereas in reality many patients visit multiple providers in multiple settings of care. Compounding the problem, most conventional electronic health record (EHR) vendors do not adhere a standard national format for quality reporting and many HER vendors cannot yet generate many of the national quality measures required by federal programs.

SUMMARY

Described embodiments herein capture quality measures for one patient in multiple settings of care (across multiple providers) and roll the measures up into one combined quality measure for that patient. Such a system provides patient-centric quality measurement and does correlate to improved outcomes for a single patient. Furthermore, disclosed embodiments also can take the quality measures for multiple patients in multiple settings of care (with multiple providers) and roll those up into a "population-centric" quality measurement that is correlated to improved outcomes for multiple patients in a population, thus helping improve population health. For example, one embodiment obtains data for multiple patients in a patient population that have common health issues (high incidence rate of diabetes) and determines how they scored on measures related to diabetes in every care setting whether they were in different clinics, cities or even different states and see how they all compare one quality measure. An illustrative embodiment strictly uses standards for quality measure information thus allowing full interoperability for quality measure reporting where none exists today.

Described embodiments herein find and combine all data necessary to compute quality measures. Conventional EHR systems are unable to do so, resulting in very high expenses for those vendors who achieve even a very basic level of success in quality reporting. For example, calculating a quality measure related to screening for breast cancer not only requires data that the EHR vendor has readily available from the in-clinic screening by the doctor, but this measure also requires data that can only be found in an electronic "lab result" and this lab result information is not easily accessible by the vast majority of HER systems; it typically resides in different places. The necessity of finding and integrating data from disparate sources is a major component to the difficulty and expense incurred by EHR vendors trying to calculate and report quality measures. To compound this matter, the federal government typically changes significant portions of the quality reporting requirements every year.

Described embodiments herein provide common, centralized quality reporting destinations. These embodiments improve the behavior of the providers but more importantly improve the health of the patient (e.g. improve outcomes). The described embodiments move away from volume-based delivery and payment to quality-based delivery and payment. The described embodiments provide a more sustainable system that the current volume-based healthcare system.

An illustrative method according to a set of instructions stored on the memory of a computing device includes receiving from a plurality of measure storage devices, by a processor of the computing device, a plurality of measures pertaining to at least one patient and at least one clinical measure of the at least one patient. Each of the plurality of measure storage devices are associated with at least one of a plurality of healthcare providers. The method further includes determining, by the processor, a patient-centered quality measure indicating quality across the plurality of healthcare providers with respect to the at least one patient and the at least one clinical measure.

An illustrative method according to a set of instructions stored on the memory of a computing device includes receiving from a plurality of measure storage devices, by a processor of the computing device, a plurality of measures pertaining to a plurality of patients and at least one clinical measure of the plurality of patients. Each of the plurality of measure storage devices are associated with at least one of a plurality of healthcare providers. The method further includes determining, by the processor, a population-centered quality measure indicating quality across the plurality of healthcare providers with respect to the plurality of patients and the at least one clinical measure.

BRIEF DESCRIPTION OF THE DRAWINGS

Illustrative embodiments will hereafter be described with reference to the accompanying drawings.

DETAILED DESCRIPTION

Figure 1:
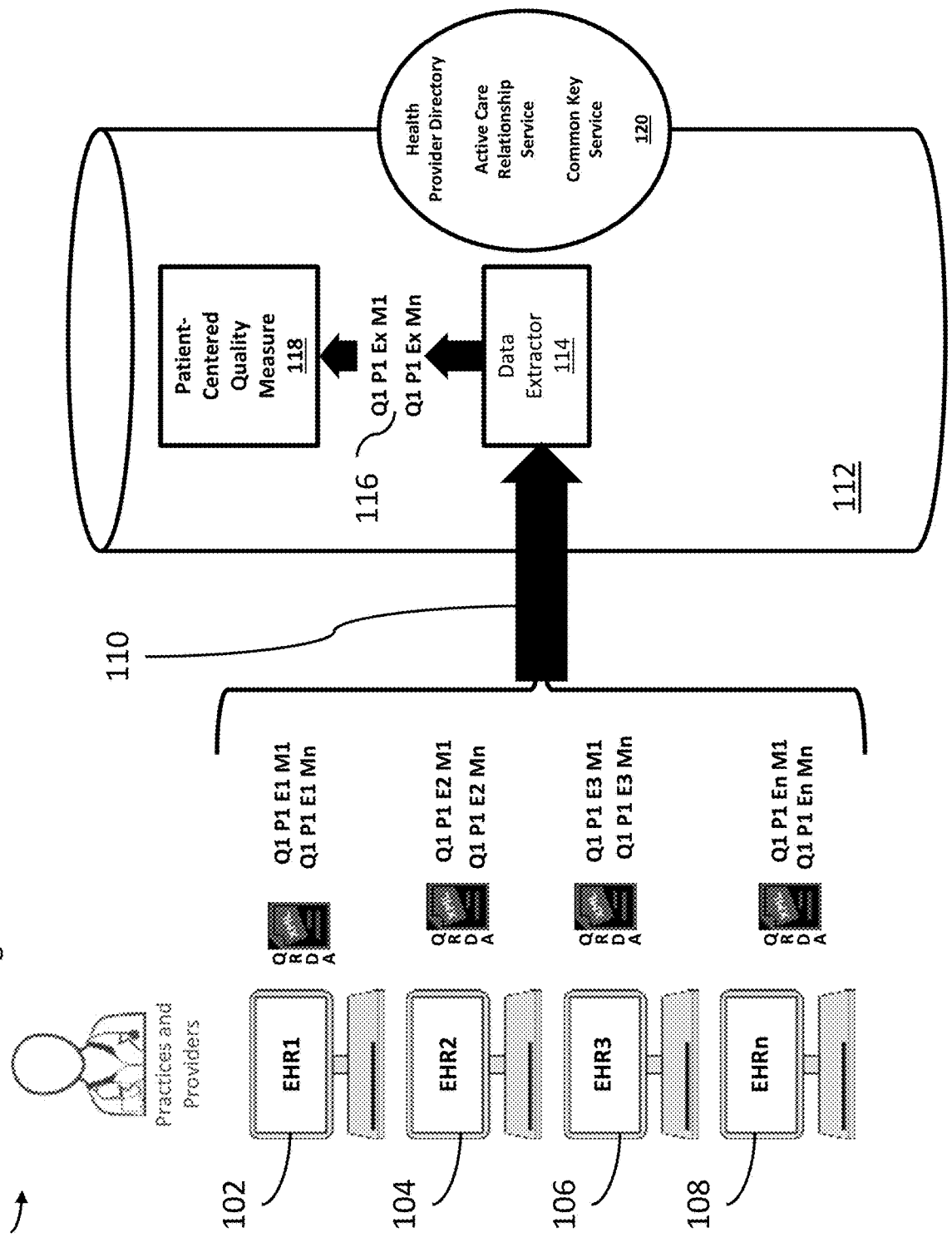
FIG. 1 is a diagram illustrating a system for quality data extraction, alignment, and reporting, including generating a patient-centered quality measure in accordance with an illustrative embodiment.

Disclosed herein are systems and methods, which can be realized in software, hardware, or a combination thereof, to perform quality data extraction, alignment, and reporting. Quality data and quality measure extraction, alignment, and reporting are useful in industries where continuous quality improvement is applied, such as manufacturing, energy, or healthcare. In healthcare for example, various types of quality measures have been established for determining the quality of care that healthcare providers deliver to their patients, and health plans/payers are shifting to payment models that reward providers based on higher quality of care delivered to the health plan's members. Advantageously, the methods and systems disclosed herein provide for extracting, calculating, aligning, and reporting quality information. Further, current quality measurements are provider-centric. The methods and systems disclosed herein advantageously demonstrate how patient-centric, as opposed to provider-centric, quality information may be extracted, calculated, and aligned. Current quality reporting includes methods and formats that vary widely by provider and payer and involve costly and inefficient point-to-point connections between every provider and every payer nationally, and provider payments from payers can be affected by the provider's quality ratings. Disclosed herein are methods and systems for a single method and service for transporting quality data in standard formats, extracting quality information from that data to calculate measures, aligning measures for one patient in multiple care settings and for populations of patients thereby offering advantageous ways for performing patient-centric quality measurement, and for reporting such quality measures to health plans and payers, including state and federal government payers such as Medicaid and Medicare.

This methods and systems disclosed herein are not limited to improvement in healthcare, but can be used for quality measurement and quality reporting in any industry where continuous quality improvement is needed.

In various healthcare related embodiments, a method is initiated when a Certified Electronic Health Record Technology (CEHRT) used by a healthcare provider when recoding information during a patient visit sends one file containing quality information in a standard format (Q1) for one patient (P1) for that one electronic health record (EHR) (E1) for one quality measure (M1)—referred to as Q1P1E1M1. Another provider seeing that same patient (P1) in a different setting might be using a different EHR (E2) and would send one quality measure in the same format (Q1) for the same measure (M1)—referred to as Q1P1E2M1. When a system as disclosed herein receives Q1P1E1M1, Q1P1E2M1, and conceivably any files containing the same measure (M1) for that patient (P1) from any number of additional EHRs and care settings (En), notated as Q1P1EnM1, the systems and methods can then: (1) align and roll-up all Q1P1M1 from any EHR/care setting (Ex) by treating the EHR number as a "don't care" giving Q1P1ExM1, resulting in a patient-centric quality measure; and (2) align and roll-up all Q1ExM1 for a population of n patients (P1 . . . n) to resulting in a population-centric quality measure.

The systems and methods disclosed herein work for any number of patients, EHRs/care settings, and quality measures, of which there are hundreds or more (denoted Q1PnEnMi). The systems and methods disclosed herein also work for other formats, such as payer proprietary formats, BPnEnMi. For example, the system can utilize, read, convert, extract, incorporate, etc. various reporting formats, such as Quality Reporting Document Architecture (QRDA), Blue Care Networks (BCN), Semantic clinical Drug Form (SCDF), or Continuity of Care Document (CCD) formats. In some embodiments, different or additional formats may be used. In some embodiments, a system includes an extractor where providers send quality data in a first format and it is extracted to one or more formats for various uses such as quality reports and/or sending to payers. For example, a system can include a BCN to QRDA extractor where providers send quality data in a BCN format. The BCN to QRDA extractor can therefore extract Q1 formatted data from BCN (B) formatted data to convert BCN (B) to QRDA 1 (Q1) to generate quality reporting. The QRDA data that has been extracted may also be sent to payers. After all processing, quality measures can be reported to health plans/payers in a QRDA 1 (Q1) format, or other format as desired. Further embodiments are described below with respect to the figures.

FIG. 1 is a diagram illustrating a system for quality data extraction, alignment, and reporting, including generating a patient-centered quality measure in accordance with an illustrative embodiment. In alternative embodiments, fewer, additional, and/or different components may be present. The system 100 includes practices and providers that use electronic health records (EHR) systems 102, 104, 106, and 108. The EHRs 102, 104, 106, 108 may be similar or different EHR systems. In this way, different types of EHRs can send quality reporting data within the system, and the system can align data from any type of EHR/practice/provider. In the system 100, the EHRs 102, 104, 106, 108 generate data in the QRDA format.

The EHR 102 generates report Q1P1E1M1, indicating QRDA data (Q1) for a first patient (P1), from the first EHR 102 (E1), about a first measure (M1). A measure may be any type of healthcare reporting data. For example, M1 may related to blood pressure, temperature, weight, etc. At the time of writing hundreds of standard measures are recorded and reported in EHRs by practices and providers that can be sent and used for quality reporting. The systems and methods herein can be adapted to accommodate as many or as few measures as desired, including measures that are not currently recorded and reported today. Any number of other measures that can be reported with respect to the first patient are indicated in the system 100 as Q1P1E1Mn. Similar data can be generated on the first patient from the other EHRs 104, 106, and 108. Such data has different E designations indicating the EHR it came from (e.g., E2, E3, En). The EHR 108 (En) represents that there can be any number of possible EHRs sending measures information. In some embodiments, multiple providers may use the same EHR. In some embodiments, a single payer may use multiple EHRs.

Measure data can be sent from the EHRs 102, 104, 106, 108 at a step 110 to a quality data processing system 112. At the quality data processing system 112, data can be extracted, aligned, and reported as disclosed herein throughout. For example, at a data extractor 114, the system can extract data 116 that is related to the first measure (M1), regardless of what EHR the data came from (denoted by Ex). In this way, all the data on the first patient (P1) related to the first measure (M1) can be extracted and aligned for a patient-centered quality measure 118. In this way, no matter which practices and providers a patient has visited, data related to the first measure (M1) can be assembled for an inclusive report on that first patient (P1). Similarly, data (Q1P1ExMn) for any other measure (Mn) can be assembled for the first patient (P1) and used for the patient-centered quality measure 118.

The quality data processing system 112 also includes aspects 120 of a health provider directory (HPD), active care relationship service (ACRS), and a common key service (CKS). Such aspects 120 can assist in reporting. For example, the HPD can used to keep track of which EHRs are associated with specific health care providers and information about those providers. In another example, the ACRS can be used to keep track of information relating to particular patients, such as demographic information. In another example, the CKS can be used to identify patients anonymously and uniquely, such that their data is protected but stays organized and separate from other patients. U.S. patent application Ser. No. 14/643,910, filed on Mar. 10, 2015, is incorporated herein by reference, and describes various aspects of a CKS system that may be utilized in combination with the systems and methods disclosed herein.

Figure 2:
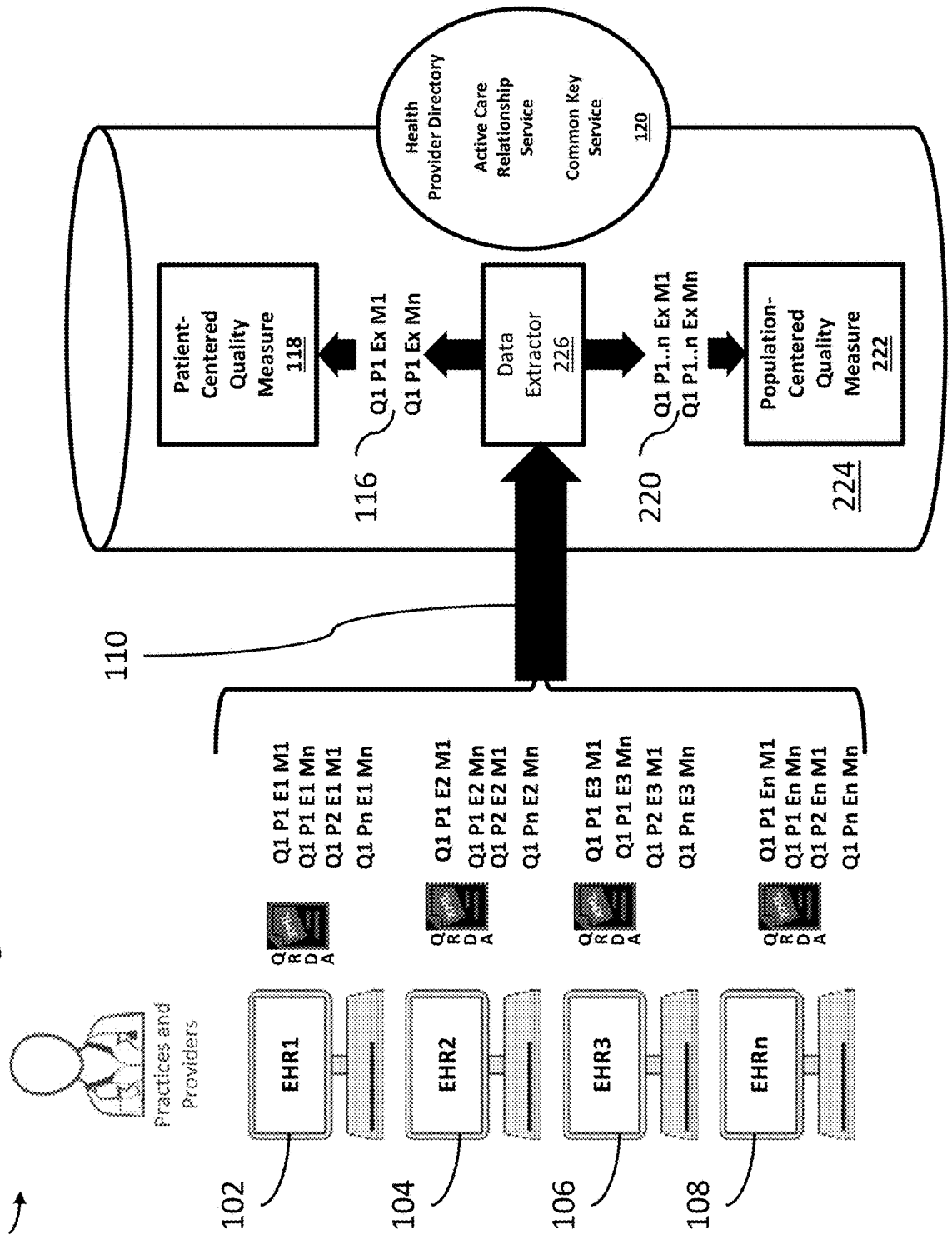
FIG. 2 is a diagram illustrating a system for quality data extraction, alignment, and reporting, including generating a population-centered quality measure in accordance with an illustrative embodiment.

FIG. 2 is a diagram illustrating a system for quality data extraction, alignment, and reporting, including generating a population-centered quality measure in accordance with an illustrative embodiment. In alternative embodiments, fewer, additional, and/or different components may be present. The system 200 includes additional data for a second patient (P2) and any number of additional patients (Pn) from each of the EHRs 102, 104, 106, 108. For example, the system 200 shows a measure (Q1P2E1M1) in QRDA format (Q1) for a second patient (P2), from the EHR 102 (E1), and relating to the first measure (M1). The measure(s) from the EHR 102 can include any number of measure for any number of other patients as shown by Q1PnE1Mn. The other EHRs 104, 106, and 108 show similar measures for the second and additional patients.

Such data can be sent to a quality data processing system 224, where a data extractor 226 can extract data 220 for population-centered quality measure reporting 222. For example, information in a QRDA format (Q1) can be extracted for a population (P1 . . . n) from any EHR (Ex) for a first measure (M1): Q1P1 . . . nExM1. A population can be selected to be all of the patients that have a particular measure reported, or may be selected based on any other category. For example, a population may be any patient who has visited a practice or provider in a certain health system, any patient that matches a certain demographic, any patient with a particular diagnosis, or any other type of population or combinations of populations. Thus, with the data Q1P1 . . . nExM1 reports can be assembled that indicate quality for a given population with respect to a first measure. Similarly, population-centered quality measures 222 may be assembled for any other populations or combinations of populations based on one or more different measure, as represented by Q1P1 . . . nExMn.

The HPD, ACRS, and CKS of 120 can also be used for rolling up different types of quality reports efficiently storing, sorting, and keeping track of data for those various reports. For example, selecting different types of populations to run reports on may be assembled by filtering for certain demographics of patients, such as location, age, gender, etc. Other types of reports may be done to focus on populations that visit certain providers, or reports that are focused on patients that visit providers with a particular EHR. Population reports for patients diagnosed similarly may also be run. Other types of reports based on various specific characteristics of a population are also contemplated herein.

Figure 3:
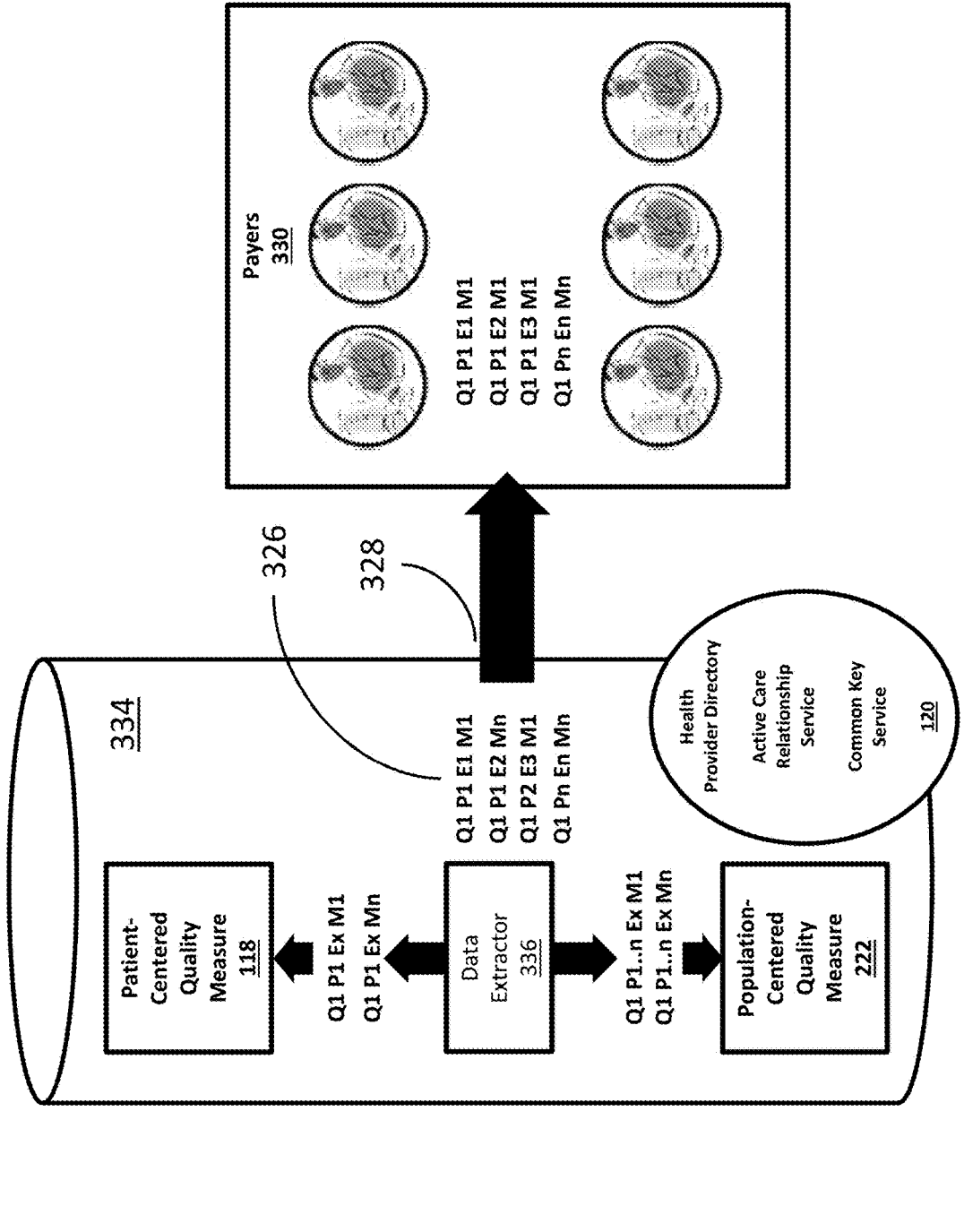
FIG. 3 is a diagram illustrating a system for quality data extraction, alignment, and reporting, including sending data to payers in accordance with an illustrative embodiment.

FIG. 3 is a diagram illustrating a system for quality data extraction, alignment, and reporting, including sending data to payers in accordance with an illustrative embodiment. In alternative embodiments, fewer, additional, and/or different components may be present. The system 300 shows how data extracted by a data extractor 336 of a quality data processing system 334 can also be sent payers 330, in addition extracted data being used to generate patient- and population-centered quality measures 118 and 222.

The data extractor 336 extracts data 326 related to a first patient (P1), a second patient (P2), and any other patients (Pn) that a payer 330 may use to determine quality measures (M1, Mn) and/or pay the practices/providers shown in FIGS. 1 and 2. Accordingly, the data 326 for any patient from any EHR related to any measure can be extracted as indicated by Q1PnEnMn. Such data 336 can be sent at 328 to various payers 330. The aspects 120 including the HPD, ACRS, and CKS may be utilized to determine what data 326 to send to particular payers 330.

Figure 4:
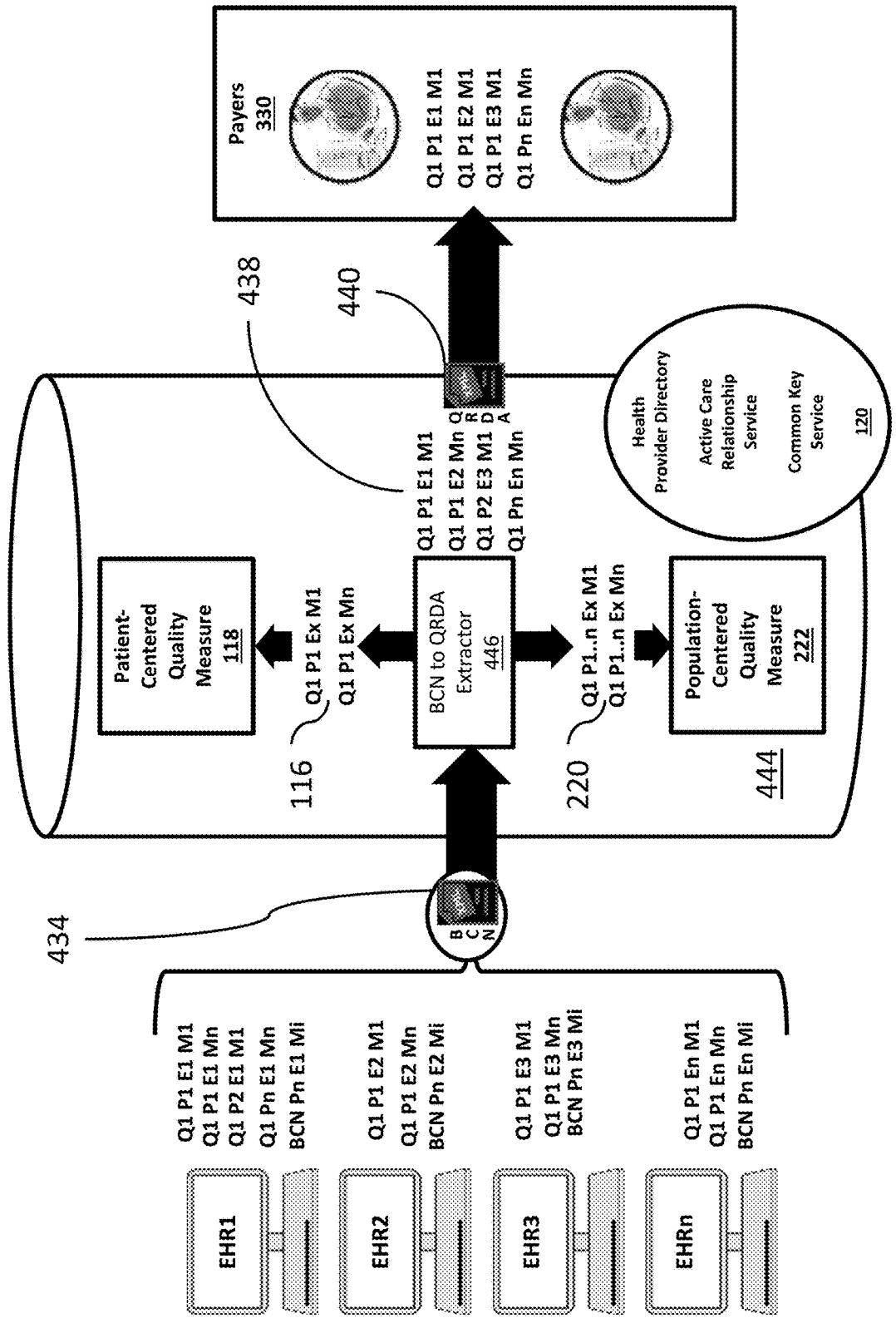
FIG. 4 is a diagram illustrating a system for quality data extraction, alignment, and reporting, including extracting and converting data in accordance with an illustrative embodiment.

FIG. 4 is a diagram illustrating a system for quality data extraction, alignment, and reporting, including extracting and converting data in accordance with an illustrative embodiment. In alternative embodiments, fewer, additional, and/or different components may be present. The system 400 shows an example where quality reporting data from EHRs is in a BCN format and converted into QRDA data formats. In various embodiments, any format may be used to send data from the EHRs and that data can be converted to any other type of format. For example, data from the first EHR relating to various patients (P1, P2, Pn) for various measures (M1, Mn) are included in BCN format measures, shown as BCNPnE1Mi. Similarly, data from the other EHRs is also sent in a BCN formatted measure, including data from EHR2, EHR3, and any other EHRs (EHRn).

The data from the EHRs is sent to a BCN to QRDA extractor 446 of a quality data processing system 444. The BCN to QRDA extractor 446 can extract QRDA data from the BCN data for use in assembling patient- and/or population-centered quality measure reports 118 and 222 as disclosed herein. The BCN to QRDA Extractor 446 can also extract QRDA data 438 to be sent in QRDA format 440 to payers 330. Therefore, the quality data processing system 444 has value where providers or EHRs send measure data that is in a different format than data that should be sent to payers. Similarly, data sent to a quality data processing system 444 can still be extracted and used to assemble patient- and/or population-centered quality measure reports 118 and 222.

In some embodiments a quality data processing system may receive measure data in various different formats (BCN, QRDQ, etc.), and various data extractors may be used to extract data into any number of formats as desired by payers and to assemble various patient- and population-centered quality measures. Accordingly, any type of format used by a payer, provider, EHR, etc. can be accommodated by the system. Similarly, any type or format of data received can be extracted, aligned, and used for quality reporting.

The systems of FIGS. 3 and 4 enable the capture of quality measures for a patient in multiple settings of care (across multiple providers). These systems can roll the measures up into one combined quality measure for that patient. Such systems provides patient-centric quality measurement that can correlate to improved outcomes for a single patient. The systems also can take the quality measures for multiple patients in multiple settings of care (with multiple providers) and roll those up into a "population-centric" quality measurement that is correlated to improved outcomes for multiple patients in a population, thus helping improve population health. For example, one embodiment obtains data for multiple patients in a patient population that have common health issues (high incidence rate of diabetes) and determines how they scored on measures related to diabetes in every care setting whether they were in different clinics, cities or even different states and see how they all compare one quality measure. An illustrative embodiment strictly uses standards for quality measure information thus allowing full interoperability for quality measure reporting where none exists today.

Calculating a quality measure related to screening for breast cancer not only requires data that the EHR vendor has readily available from the in-clinic screening by the doctor, but this measure also requires data that can only be found in an electronic "lab result" and this lab result information is not easily accessible by the vast majority of HER systems; it typically resides in different places. The necessity of finding and integrating data from disparate sources is a major component to the difficulty and expense incurred by EHR vendors trying to calculate and report quality measures. The systems of FIGS. 3 and 4 common, centralized quality reporting destinations. These systems improve the behavior of the providers but more importantly improve the health of the patient (e.g. improve outcomes). Advantageously, the systems move away from volume-based delivery and payment to quality-based delivery and payment.

Figure 5:
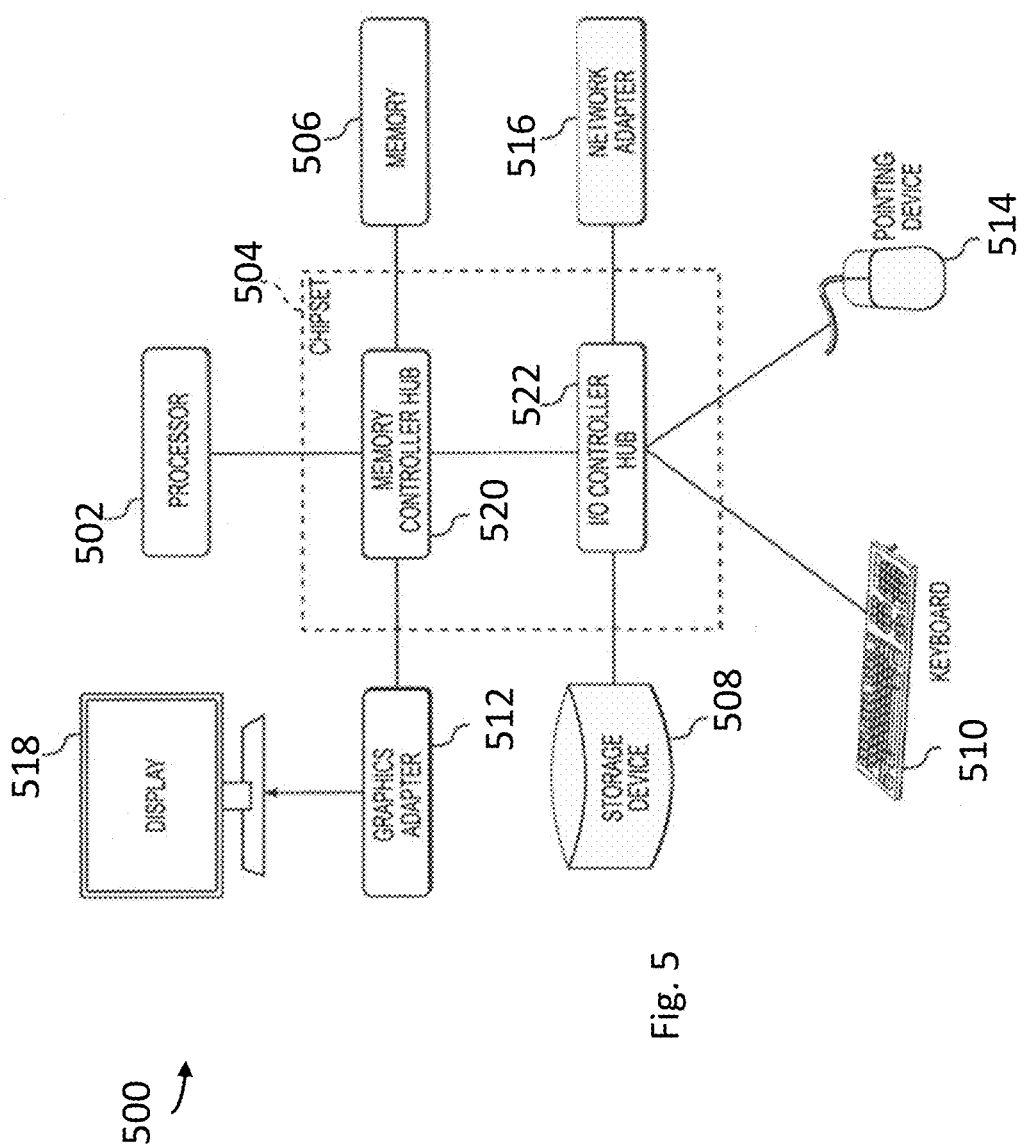
FIG. 5 is a block diagram illustrating an example computer 500 in accordance with an illustrative embodiment.

FIG. 5 is a block diagram illustrating an example computer 500 in accordance with an illustrative embodiment. In alternative embodiments, fewer, additional, and/or different components may be present. The computer 500 may be any computing machine, such as a tablet, smart phone, laptop computer, desktop computer, server, remote client device, gaming device, smart television device, wearable computer, or any combination thereof. The computer 500 includes at least one processor 502 coupled to a chipset 504. The chipset 504 includes a memory controller hub 520 and an input/output (I/O) controller hub 522. A memory 506 and a graphics adapter 512 are coupled to the memory controller hub 520, and a display 518 is coupled to the graphics adapter 512. A storage device 508, keyboard 510, pointing device 514, and network adapter 516 are coupled to the I/O controller hub 522. Other embodiments of the computer 500 may have different architectures.

The storage device 508 is a non-transitory computer-readable storage medium such as a hard drive, compact disk read-only memory (CD-ROM), DVD, or a solid-state memory device. The memory 506 holds instructions and data used by the processor 502. The pointing device 514 is a mouse, track ball, or other type of pointing device, and is used in combination with the keyboard 510 to input data into the computer 500. The pointing device 514 may also be a gaming system controller, or any type of device used to control the gaming system. For example, the pointing device 514 may be connected to a video or image capturing device that employs biometric scanning to detect a specific user. The specific user may employ motion or gestures to command the point device 514 to control various aspects of the computer 500.

The graphics adapter 512 displays images and other information on the display 518. The network adapter 516 couples the computer system 500 to one or more computer networks.

The computer 500 is adapted to execute computer program modules for providing functionality described herein. As used herein, the term module refers to computer program logic used to provide the specified functionality. Thus, a module can be implemented in hardware, firmware, and/or software. In one embodiment, program modules are stored on the storage device 508, loaded into the memory 506, and executed by the processor 502.

The types of computers used by the entities and processes disclosed herein can vary depending upon the embodiment and the processing power required by the entity. The computer 500 may be a mobile device, tablet, smartphone or any sort of computing element with the above-listed elements. For example, a data storage device, such as a hard disk, solid state memory or storage device, might be stored in a distributed database system comprising multiple blade servers working together to provide the functionality described herein. The computers can lack some of the components described above, such as keyboards 510, graphics adapters 512, and displays 518.

The computer 500 may act as a server. The computer 500 may be clustered with other computer 500 devices to create the server. The various computer 500 devices that constitute the server may communicate with each other over a network.

As would be appreciated by one of ordinary skill in the art, the embodiments disclosed herein may be implemented on any system, network architecture, configuration, device, machine, or apparatus, and is not to be construed as being limited to any specific configuration, network, or systems, even though an example system is shown and described with respect to FIG. 5. The embodiments herein may be suitably implemented on conventional computing devices, for example, computer workstations, on Internet based applications, on optical computing devices, neural computers, biological computers, molecular computing devices, and other devices. As may be appreciated by those skilled in the art, the present invention, in short, may be implemented on any system, automaton, and/or Turing machine.

An automaton is herein described as a mechanism that is relatively self-operating and designed to follow a predetermined sequence of operations or respond to encoded instructions. A Turing machine is herein described as an abstract expression of a computing device that may be realized or implemented on an infinite number of different physical computing devices. Examples of systems, automatons and/or Turing machines that may be utilized in performing the process of the present invention include, but are not limited to: electrical computers (for example, an International Business Machines (IBM) personal computer); neuro-computers (for example, one similar to the "General Purpose Neural Computer" described in U.S. Pat. No. 5,155,802, issued to Paul H. Mueller, on Oct. 13, 1992); molecular computers (for example, one similar to the "Molecular Automata Utilizing Single or Double-Strand Oligonucleotides" described in U.S. Pat. No. 5,804,373, issued to Allan Lee Schweiter et al., on Sep. 8, 1998); biological computers (for example, one similar to the biological computer presented by Ehud Shapiro, of the Computer Science and Applied Mathematics Department at the Weizman Institute of Science (Rehovot, Israel), at the Fifth International Meeting on DNA-Based Computers); and optical computers. For purposes of simplicity, such devices hereinafter are referred to as computers, as is commonly understood in the art. But, the embodiments disclosed herein are not limited being applied to such devices and may be accomplished upon any system or collection of systems capable of providing the features and functions identified herein.

The methods and systems described above and below with respect to FIGS. 1-4 may be performed partially or wholly on a processor, such as the one described above with regards to computer 500.

Certain of the devices shown in FIG. 5 include a computing system. The computing system includes a processor (CPU) and a system bus that couples various system components including a system memory such as read only memory (ROM) and random access memory (RAM), to the processor. The aspects disclosed herein may be suitably implemented on conventional computing devices, for example, computer workstations, on Internet based applications, on optical computing devices, neural computers, biological computers, molecular computing devices, and other devices. As may be appreciated by those skilled in the art, the aspects disclosed herein may be implemented on any system, automaton, and/or automated machine.

Other system memory may be available for use as well. The computing system may include more than one processor or a group or cluster of computing system networked together to provide greater processing capability. The system bus may be any of several types of bus structures including a memory bus or memory controller, a peripheral bus, and a local bus using any of a variety of bus architectures. A basic input/output (BIOS) stored in the ROM or the like, may provide basic routines that help to transfer information between elements within the computing system, such as during start-up. The computing system further includes data stores, which maintain a database according to known database management systems. The data stores may be embodied in many forms, such as a hard disk drive, a magnetic disk drive, an optical disk drive, tape drive, or another type of computer readable media which can store data that are accessible by the processor, such as magnetic cassettes, flash memory cards, digital versatile disks, cartridges, random access memories (RAMs) and, read only memory (ROM). The data stores may be connected to the system bus by a drive interface. The data stores provide nonvolatile storage of computer readable instructions, data structures, program modules and other data for the computing system.

To enable human (and in some instances, machine) user interaction, the computing system may include an input device, such as a microphone for speech and audio, a touch sensitive screen for gesture or graphical input, keyboard, mouse, motion input, motion detection, camera for video and photo input, and so forth. An output device can include one or more of a number of output mechanisms, such as a display screen, a printer, or speaker. In some instances, multimodal systems enable a user to provide multiple types of input to communicate with the computing system. A communications interface generally enables the computing device system to communicate with one or more other computing devices using various communication and network protocols.

Embodiments disclosed herein can be implemented in digital electronic circuitry, or in computer software, firmware, or hardware, including the herein disclosed structures and their equivalents. Some embodiments can be implemented as one or more computer programs, i.e., one or more modules of computer program instructions, encoded on a tangible computer storage medium for execution by one or more processors. A computer storage medium can be, or can be included in, a computer-readable storage device, a computer-readable storage substrate, or a random or serial access memory. The computer storage medium can also be, or can be included in, one or more separate tangible components or media such as multiple CDs, disks, or other storage devices. The computer storage medium does not include a transitory signal.

As used herein, the term processor encompasses all kinds of apparatus, devices, and machines for processing data, including by way of example a programmable processor, a computer, a system on a chip, or multiple ones, or combinations, of the foregoing. The processor can include special purpose logic circuitry, e.g., an FPGA (field programmable gate array) or an ASIC (application-specific integrated circuit). The processor also can include, in addition to hardware, code that creates an execution environment for the computer program in question, e.g., code that constitutes processor firmware, a protocol stack, a database management system, an operating system, a cross-platform runtime environment, a virtual machine, or a combination of one or more of them.

A computer program (also known as a program, module, engine, software, software application, script, or code) can be written in any form of programming language, including compiled or interpreted languages, declarative or procedural languages, and the program can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

To provide for interaction with an individual, the herein disclosed embodiments can be implemented using an interactive display, such as a graphical user interface (GUI). Such GUI's may include interactive features such as pop-up or pull-down menus or lists, selection tabs, and other features that can receive human inputs.

The computing system disclosed herein can include clients and servers. A client and server are generally remote from each other and typically interact through a communications network. The relationship of client and server arises by virtue of computer programs running on the respective computers and having a client-server relationship to each other. In some embodiments, a server transmits data (e.g., an HTML page) to a client device (e.g., for purposes of displaying data to and receiving user input from a user interacting with the client device). Data generated at the client device (e.g., a result of the user interaction) can be received from the client device at the server.

In an illustrative embodiment, any of the operations described herein can be implemented at least in part as computer-readable instructions stored on a computer-readable medium or memory. Upon execution of the computer-readable instructions by a processor, the computer-readable instructions can cause a computing device to perform the operations.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. A method according to a set of instructions stored on a memory of a computing device, the method comprising:
   receiving from a plurality of electrical health record systems, at a quality data processing system, a plurality of measures, wherein each measure of the plurality of measures pertains to a same patient and a same clinical measure, and wherein each measure of the plurality of measures is:
      received from a respective one of the plurality of electrical health record systems; and
      generated by a respective one of a plurality of healthcare providers that is associated with the respective one of the plurality of electrical health record systems for the same clinical measure of that same patient during a visit by the same patient to the respective healthcare provider;
   extracting, at the quality data processing system and using an active care relationship service, a common key service, and a healthcare provider directory tracking which health record systems of the plurality of health record systems are associated with each healthcare provider of the plurality of healthcare providers, a subset of the plurality of measures associated with a subset of the plurality of healthcare providers with respect to the patient and the same clinical measure of that patient, wherein the active care relationship service is used to keep track of information relating to a plurality of patients, wherein the common key service is used to identify the patient out of the plurality of patients anonymously and uniquely;
   calculating, based on the extracted subset of the plurality of measures, a patient-centered quality measure indicating quality across the subset of the plurality of healthcare providers with respect to the same patient and the same clinical measure of that patient; and
   transmitting from the quality data processing system to at least one payer device via a computer network, the patient-centered quality measure.

2. The method of claim 1, wherein the plurality of measures are formatted according to a Quality Reporting Document Architecture (QRDA) format.

3. The method of claim 1, further comprising determining one combined quality measure for the patient.

4. The method of claim 1, further comprising determining quality measures for a plurality of patients in multiple settings of care with the healthcare providers using the healthcare provider directory.

5. The method of claim 4, further comprising calculating a population-centered quality measuring outcomes for multiple patients in a population.

6. The method of claim 4, wherein the quality measures are based on standards-based quality measure information configured to be communicated to a plurality of systems that are configured to receive the quality measures from the quality data processing system.

7. The method of claim 1, where the plurality of measures comprise data necessary to compute quality measures.

8. The method of claim 1, further comprising obtaining data for multiple patients in a patient population with common health issues and determining how the multiple patients scored on measures related to the common health issues in every care setting by clinic, city and state.

9. A method according to a set of instructions stored on a memory of a computing device, the method comprising:
   receiving from a plurality of electrical health record systems, at a quality data processing system, a plurality of measures pertaining to a plurality of patients and a same clinical measure of the plurality of patients, wherein each measure of the plurality of measures is:
      received from a respective one of the plurality of electrical health record systems; and
      generated by a respective one of a plurality of healthcare providers that is associated with the respective one of the plurality of electrical health record systems for the same clinical measure of a respective one of the plurality of patients during a visit by the respective patient to the respective healthcare provider;
   extracting, at the quality data processing system and using an active care relationship service, a common key service, and a healthcare provider directory tracking which health record systems of the plurality of health record systems are associated with each healthcare provider of the plurality of healthcare providers, a subset of the plurality of measures associated with a subset of the plurality of healthcare providers with respect to the plurality of patients and the same clinical measure, wherein the active care relationship service is used to keep track of information relating to the plurality of patients, wherein the common key service is used to identify a patient out of the plurality of patients anonymously and uniquely;
   calculating, based on the extracted subset of the plurality of measures, a population-centered quality measure indicating quality across the subset of the plurality of healthcare providers with respect to the plurality of patients and the same clinical measure; and
   transmitting from the quality data processing system to at least one payer device via a computer network, the population-centered quality.

10. The method of claim 9, wherein the plurality of measures are formatted according to a Quality Reporting Document Architecture (QRDA) format.

11. The method of claim 9, wherein the plurality of measures are formatted according to a Blue Care Network (BCN) format.

12. The method of claim 11, further comprising converting the plurality of measures from the BCN format to a Quality Reporting Document Architecture (QRDA) format.

13. The method of claim 12, further comprising sending the plurality of measures converted to the QRDA format to a plurality of payer devices.

14. The method of claim 9, wherein the plurality of measures comprises a common key that uniquely identifies each of the plurality of patients.

15. An apparatus comprising:
a memory;
a hardware processor coupled to the memory; and
a set of instructions stored on the memory and configured to be executed by the hardware processor, wherein the hardware processor is configured to:
receive from a plurality of electrical health record systems, at a quality data processing system, a plurality of measures, wherein each measure of the plurality of measures pertains to a same patient and a same clinical measure, and wherein each measure of the plurality of measures is:
received from a respective one of the plurality of electrical health record systems; and
generated by a respective one of a plurality of healthcare providers that is associated with the respective one of the plurality of electrical health record systems for the same clinical measure of that same patient during a visit by the same patient to the respective healthcare provider;
extract, at the quality data processing system and using an active care relationship service, a common key service, and a healthcare provider directory tracking respective health record systems of the plurality of health record systems are associated with each healthcare provider of the plurality of healthcare providers, a subset of the plurality of measures associated with a subset of the plurality of healthcare providers with respect to the same patient and the same clinical measure, wherein the active care relationship service is used to keep track of information relating to a plurality of patients, and wherein the common key service is used to identify the patient out of the plurality of patients anonymously and uniquely;
calculate, based on the extracted subset of the plurality of measures, a patient-centered quality measure indicating quality across the subset of the plurality of healthcare providers with respect to the same patient and the same clinical measure of that patient; and
transmit, from the quality data processing system to at least one payer device via a computer network, the patient-centered quality measure.

16. The apparatus of claim 15, wherein the hardware processor is further configured to calculate one combined quality measure for the patient.

17. The apparatus of claim 15, wherein the hardware processor is further configured to calculate quality measures for a plurality of patients in multiple settings of care with the healthcare providers using the healthcare provider directory.

18. The apparatus of claim 17, wherein the hardware processor is further configured to calculate a population-centered quality measuring outcomes for multiple patients in a population.

19. The apparatus of claim 17, wherein the quality measures are based on standards-based quality measure information configured to be communicated to a plurality of systems that are configured to receive the quality measures from the quality data processing system.

20. The apparatus of claim 15, wherein the hardware processor is further configured to obtain data for multiple patients in a patient population with common health issues and determine how the multiple patients scored on measures related to the common health issues in every care setting by clinic, city and state.

* * * * *